Figure 1:
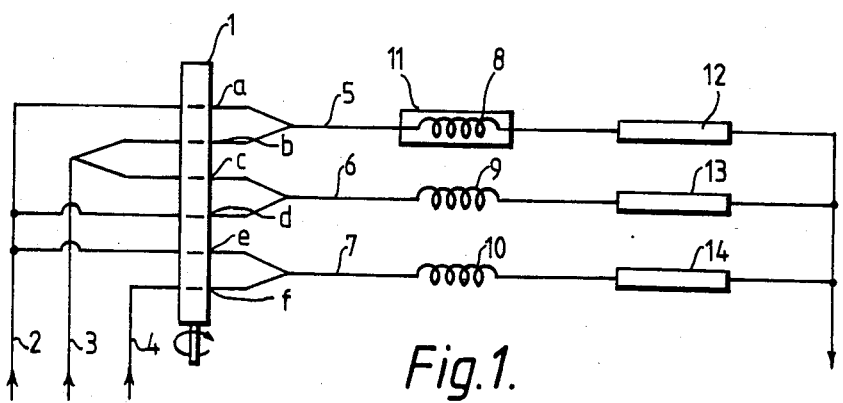

United States Patent [19]

Williams

[11] Patent Number: 4,680,271

[45] Date of Patent: Jul. 14, 1987

[54] PROCESS AND APPARATUS FOR ANALYSIS

[75] Inventor: John Williams, Mt. Helens, England

[73] Assignee: Interox Chemicals Limited, London, England

[21] Appl. No.: 693,295

[22] Filed: Jan. 22, 1985

[30] Foreign Application Priority Data

Jan. 21, 1984 [GB] United Kingdom ................ 8401630

[51] Int. Cl.$^4$ .................. G01N 21/78; G01N 21/85; G01N 35/08; G05D 21/00

[52] U.S. Cl. ........................................ 436/55; 422/13; 422/62; 422/81; 422/93; 436/50; 436/52; 436/129; 436/135; 436/158

[58] Field of Search ............ 436/50, 52, 53, 135, 436/158, 129, 55; 422/81, 82, 93, 3, 62

[56] References Cited

U.S. PATENT DOCUMENTS

| | | | |
|---|---|---|---|
| 1,681,047 | 8/1928 | Porter | 422/93 |
| 3,098,717 | 7/1963 | Ferrari, Jr. | 422/82 |
| 3,300,282 | 1/1967 | Risk et al. | 436/158 |
| 3,367,849 | 2/1968 | Blaedel et al. | 422/81 |
| 3,560,161 | 2/1971 | Webb | 422/81 |
| 3,937,615 | 2/1976 | Clack et al. | 422/62 |
| 4,248,795 | 2/1981 | Chan | 569/255 |
| 4,486,097 | 12/1984 | Riley | 422/82 |
| 4,543,637 | 9/1985 | Smith et al. | 422/62 |

Primary Examiner—Barry S. Richman
Assistant Examiner—C. M. Delahunty
Attorney, Agent, or Firm—Larson and Taylor

[57] ABSTRACT

A continuous process and apparatus for the analysis of a sample containing a peroxycompound in the presence of hydrogen peroxide using known colorimetric techniques, characterized in that a sample is taken continuously, is continuously mixed with a colorimetric reagent and is divided into two streams, and continuous differential colorimetric analysis of the two streams is effected to provided a differential signal, further characterized in that one such stream is heated to such a temperature that the peroxycompound reacts with the colorimetric reagent prior to effecting the differential colorimetric analysis, whereby the differential signal is a measure of the concentration of such peroxycompound. The process and apparatus may be modified in that a third stream is taken not containing any colorimetric reagent, and two differential colorimetric analyses are effected, whereby a further signal is obtained which is a measure of the concentration of the hydrogen peroxide. A control process using a differential signal produced by the process or apparatus may be used to control the addition of peroxycompound to the body from which the sample is taken.

19 Claims, 3 Drawing Figures

PROCESS AND APPARATUS FOR ANALYSIS

The present invention relates to a process and apparatus for analysing and also to a process and apparatus for effecting control in dependence upon the data generated as a result of such analysis.

More specifically the present invention relates to a process for the analysis of solutions containing percompounds in the presence of hydrogen peroxide. It also provides apparatus for such purposes and control processes and apparatus.

It is known that hydrogen peroxide will react at room temperature with colorimetric reagents to develop a coloured solution of which the colour intensity depends upon the concentration of hydrogen peroxide. Similarly it is known that certain peroxycompounds, specifically peracetic acid, do not react to any significant extent with such colorimetric reagents at room temperature but require to be heated to a temperature such as 90° C. before the full colour is developed.

It is an object of the present invention to provide a process and apparatus based upon the above statements.

According to the present invention there is provided a continuous process for the analysis of a sample containing a peroxycompound in the presence of hydrogen peroxide using known colorimetric techniques, characterised in that a sample is taken continuously, is continuously mixed with a colorimetric reagent and is divided into two streams, and effecting continuous differential colorimetric analysis of the two streams to provide a differential signal, further characterised in that one such stream is heated to such a temperature that the peroxycompound and the hydrogen peroxide react with the colorimetric reagent prior to effecting the differential colorimetric reagent prior to affecting the differential colorimetric analysis, whereby the differential signal is a measure of the concentration of such peroxycompound.

According to a further aspect of the present invention there is provided a control process comprising effecting analysis for a peroxycompound by a process as above specified and thereafter deriving a control signal dependent on the differential colorimetric determination, whereby the concentration of the peroxycompound can be controlled.

According to yet a further aspect of the present invention there is provided apparatus for the continuous analysis of a peroxycompound in the presence of hydrogen peroxide comprising means continuously to select a sample to be analysed, means continuously to select an aliquot of a colorimetric reagent, means continuously to mix such aliquot with the sample to provide a characteristically coloured solution, means continuously to heat a portion of such coloured solution and means continuously to effect a differential colorimetric determination on the two portions of the coloured solution.

Finally, according to yet a further aspect of the present invention there is provided control apparatus wherein the means to effect a differential colorimetric determination are used to derive a control signal dependent on the concentration of the peroxycompound such that it can be used to control such concentration.

It will be appreciated that if it is desired to effect the analysis in such a way as to give separate determinations of the peroxycompound and hydrogen peroxide this is most conveniently effected by introducing a third stream comprising the sample without the colorimetric reagent and effecting two differential colorimetric determinations.

It will also be understood that the sample can be divided into two streams either before or after it has been mixed with the colorimetric reagent and that the two streams are not required to have an equal volume flow, nor to have the same concentration of colorimetric reagent, provided that suitable compensation is made.

As will be appreciated the essence of the invention resides in conducting the colorimetric determination at two difference temperatures, namely one at which the hydrogen peroxide reacts with the colorimetric reagent and the other at which both the hydrogen peroxide and the peroxycompound react with the colorimetric reagent.

Examples of peroxycompounds to which the invention may be applied are peracetic acid and similar peroxyacids. These are widely used for disinfection purposes where there is a need to provide control of the concentration of peroxycompound in order to ensure that adequate disinfection takes place. Similarly, the invention can be applied to a wide range of solutions of organic and inorganic percompounds such as persulphates, salts of organic peroxyacids, alkyl peroxides, ketone peroxides and the like. It is clearly not necessary that the solvent is water provided that a suitable colorimetric reagent can be selected. Typical examples of colorimetric reagents, suitable for use in aqueous solution, are sodium molybdate and potassium titanium oxalate. Other colorimetric reagents which can be considered for the determination of peroxy compounds include iodides, phenolphthalin, ferrous-iron in the presence of thiocyanates, cobaltous ions in the presence of bicarbonate and other reagents known in the art.

The temperature to which the mixture is heated will normally be below 100° C., but the precise temperature will depend to some extent on the nature of the peroxycompound, the solvent used and the precise colorimetric reagent. In the specific case of peracetic acid and sodium molybdate a temperature in the range 90°–95° C. is very suitable.

As is conventional in the art, the colorimetric determination is carried out by passing a beam of light, preferably derived from a beam splitter, through two colorimetric cells and measuring the absorption of light due to the developed colour by some photosensitive device such as a silicon diode photodetector. A conventional dual-beam spectrophotometer may of course be used and in such case will normally contain irises, filters and desirably an interference filter in order to restrict the wave-length of measured light to that most strongly absorbed by the coloured solution. The changes necessary to devise a triple beam instrument will be clear to those skilled in the art.

It is preferred to use a four-chamber peristaltic pump in order to ensure that constant volumes of the sample and colorimetric reagent are passed to two mixing devices, which may be lengths of tubing, one of which is located in a heated chamber, before passing to the optical cells of the spectrophotometer. If simultaneous determination of the hydrogen peroxide content is required then a six-chamber peristaltic pump can be used and either a triple beam spectrophotometer or two dual beam devices can be used.

Figure 2:
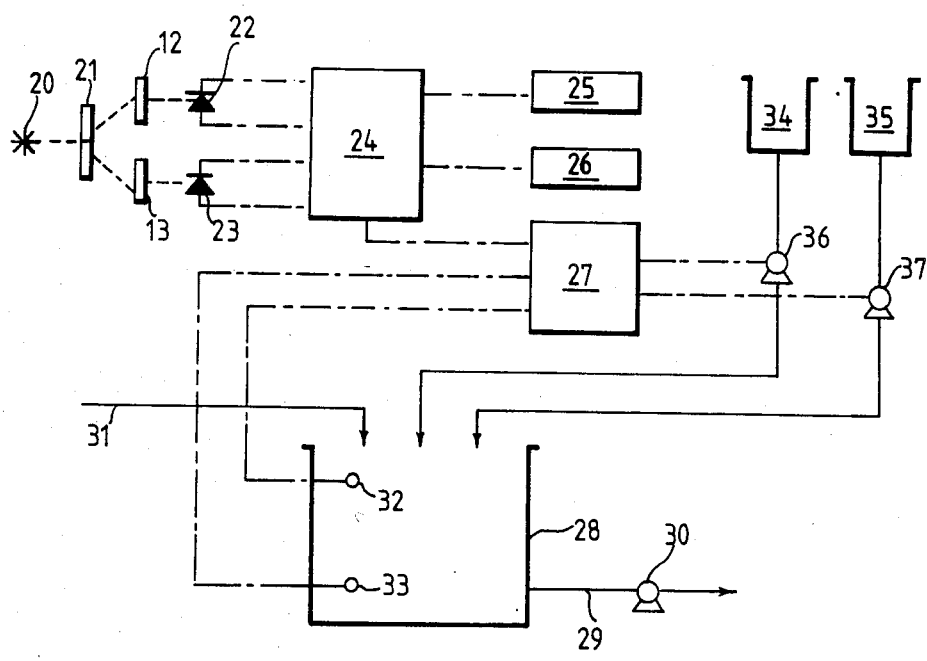
Figure 3:
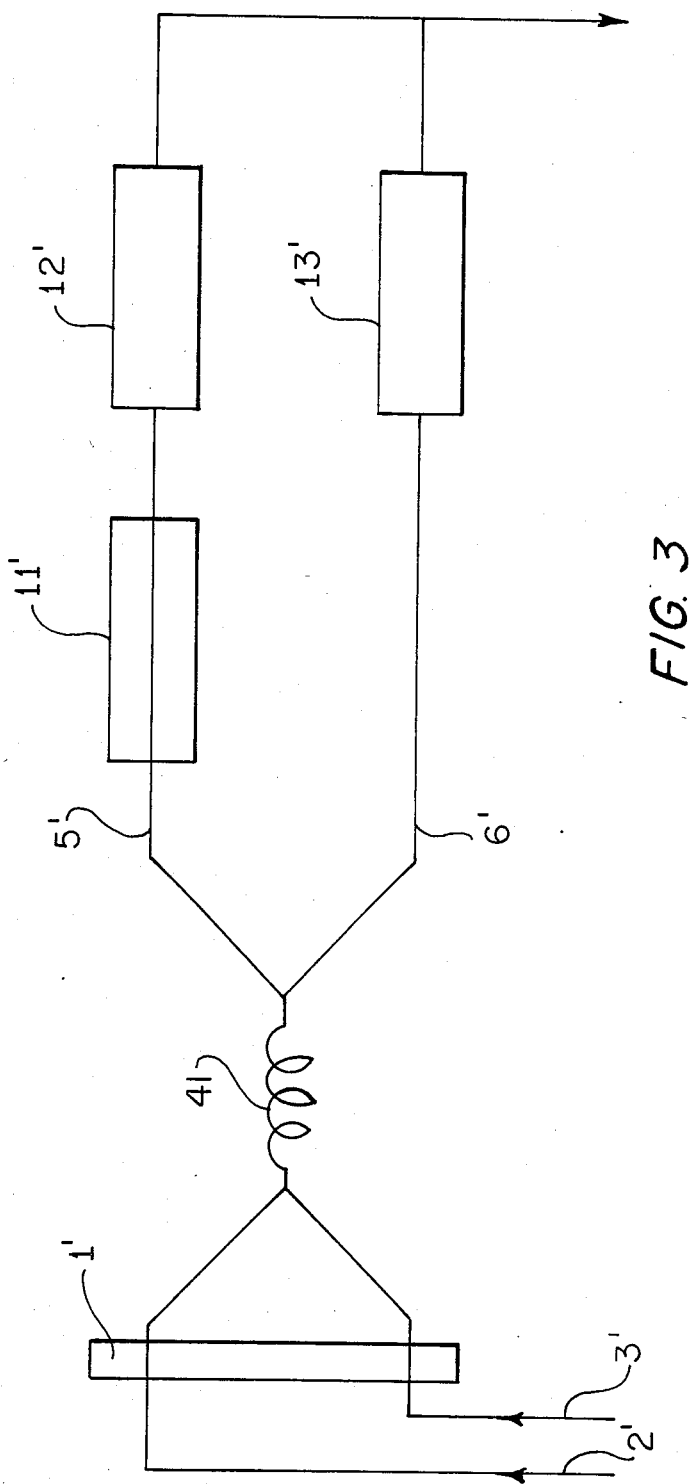

In order that the invention may more readily be understood one embodiment of the same will now be described by way of example and with reference to the accompanying drawings, in which:

FIG. 1 illustrates, in diagramatic form, apparatus for analysis in accordance with the invention, FIG. 2 illustrates, in diagramatic form, apparatus for control, and FIG. 3 is a diagrammatic flow sheet of an embodiment of the invention in which the sample stream is split after mixing with colorimetric reagent.

Referring now to FIG. 1 of the drawings, a peristaltic pump 1 having six ports, a, b, c, d, e and f is rotated at a constant speed in order to deliver constant volumes of reagent. The solution to be analysed is passed to a pipe 2 where it is split into three streams respectively connected to the ports a, d and e of the peristaltic pump 1. If necessary the stream of liquid to be analysed is passed through suitable filter means in order to remove suspended solids and the usual precautions are taken to ensure that the sample supplied at the point 2 is a representative sample. A solution of sodium molybdate in dilute sulphuric acid is supplied to a pipe 3 and is drawn by the pump 1 to ports b and c. A solution of sulphuric acid of equal concentration to the sulphuric acid in the sodium molybdate solution is drawn by the pump from a line 4 to port f.

The ports a and b, c and d, e and f are joined together in pairs as indicated in order to feed lines 5, 6 and 7 respectively. These lines in turn feed mixing coils 8, 9 and 10 of identical dimensions, coils 9 and 10 being at room temperature whilst coil 8 is located in a heated enclosure 11 which maintains it in the range 90°–95° C. In the arrangement shown, a triple beam spectrophotometer is used such that line 5 feeds cell 12, line 6 feeds cell 13 and line 7 feeds cell 14. From the cells the lines pass to waste.

For many purposes, it is not necessary to know the concentration of hydrogen peroxide and therefore only a four-port pump is needed, having the ports a, b, c and d as above described. Lines 4 and 7, the coil 10 and the cell 14 are not needed. Only a dual beam spectrophotometer is needed.

The electronic circuitry associated with the spectrophotometer is not important but will be described briefly for the sake of completion. It comprises, for a dual beam spectrophotometer, in addition to the photodiode associated with each cell, two identical logarithmic converters, a differencing amplifier and a variable gain amplifier. The currents induced in the photodiodes by light from the photometer section are converted to voltages which are proportional to the logarithms of the current and this is done for both channels. The difference in voltages is then extracted and amplified and displayed on a liquid crystal display. It is proportional to the logarithm of the ratio of the two light intensities. The triple beam device utilises additional logarithmic converters and amplifiers which enable both hydrogen peroxide an peracetic acid to be measured.

In order to set up the device, a sodium molybdate solution containing sulphuric acid of known and appropriate concentration is prepared and is supplied to line 3. A solution containing a similar amount of sulphuric acid is prepared and supplied to line 4. Demineralised water is passed to line 2. After the instrument has stabilised, the zero adjustments for both channels are adjusted so as to give a reading of zero. The supply of demineralised water to line 2 is now replaced by a supply of a standardised solution of hydrogen peroxide to and the instrument again allowed to come to equilibrium. The gain control corresponding to cells 13, 14 is now adjusted so that the display shows the correct concentration of hydrogen peroxide. The supply of hydrogen peroxide to line 2 is now interrupted and is replaced by the supply of a known solution containing peracetic acid and hydrogen peroxide whereupon the gain of corresponding to cells 12, 13 is adjusted so as to give a correct read out of the concentration of peracetic acid.

Only one standardisation point is necessary when working with solutions where there is known to be a linear relationship between peroxide concentration and colour intensity (e.g. dilute peroxide solutions). More than one standardisation point may be necessary if the relationship between peroxide concentration and colour intensity is non-linear. In order to facilitate standardisation, one normally tries to select sample/reagent volumes such that the relationship between peroxide concentration and colour intensity is linear.

It should be noted that, whilst the spectrophotometer is most sensitive and accurate when measuring the colour intensity of relatively dilute peroxide solutions, this does not mean that sample solutions containing high levels of peroxide/peracetic acid cannot be satisfactorily analysed. Thus, to those skilled in the art, it will be evident that samples containing relatively high levels of peroxide/peracetic acid can be suitably diluted before colour development either by suitable adjustment of the relative flow rates of sample and reagent, e.g. by using tubing of different diameters in the peristaltic pump, or if necessary, sample solutions containing high levels of peroxide/peracetic acid can be diluted with demineralised water (metered by the same peristaltic pump) before being mixed with reagent solution.

The instrument is now set up, and the unknown solution to be analysed is supplied to line 2 in place of the standard solution. When the instrument has reached a steady reading the displays will show the concentration of hydrogen peroxide and of peracetic acid separately.

Clearly signals corresponding to the displays can be used as control signals, for example to maintain constant the concentration of peracetic acid in a disinfecting solution.

Thus, a typical example of the use of the invention is for the control of the concentration of peracetic acid in brewery sterilising liquors where there is a requirement for a stock tank of dilute peracetic acid to be maintained. This peracetic acid solution is pumped to various fermentation vessels which need to be sterilised and during the sterilising operation some of the peracetic acid is consumed. On being returned to the stock tank, additional peracetic acid must be added to maintain the pre-determined level and concentration, the concentration of hydrogen peroxide being unimportant.

Such an arrangement will now be described with reference to both FIG. 1 and FIG. 2, using a four-port variant of FIG. 1 and a single dual-beam spectrophotometer (Interox Model 282). Control signal lines are shown chain dotted for clarity.

As shown in FIG. 2, the spectrophotometer comprises a light source 20, beam splitter 21, photodiodes 22 and 23 (associated respectively with the cells 12 and 13). The associated converters and amplifiers are shown at 24. The output from the amplifiers 24 feeds a liquid crystal display 25, a chart recorder 26 and a control unit 27.

The peracetic acid is contained in a stock tank 28 from which it is pumped via line 29 by a pump 30 to the vessels to be sterilised (not shown) and returned to the tank 28 by a line 31. The stock tank 28 contains high and low level sensors 32 and 33, connected to the control unit 27.

Make-up peracetic acid is contained in a tank 34 and make-up water in a tank 35. The control unit 27 controls metering pumps 36 and 37 to supply peracetic acid and water to the tank 29 when the level sensors 32 and 33 show that it is necessary, the respective proportions being determined by the control unit 27 in response to the signals from the amplifiers 24.

In use, the sample of a solution of dilute peracetic acid in the sterilant tank 28 is drawn through line 2 (see FIG. 1) to ports a and d of the pump. The reagent solution contains 10 g/l sodium molybdate and 10 g/l sulphuric acid and is drawn to ports b and c of the pump. The pump operates so that the flow through each port is 0.5 ml/min. The coils 8 and 9 are identical and dimensioned so that line 5 is heated by the enclosure 11 to 90°-95° C. for about 2 minutes before reaching cell 12.

The spectrophotometer is initially calibrated with a standard solution of peracetic acid (300 mg/l) and is thereafter allowed to run continuously with sample solution. The difference in colour intensity of the solutions passing through the optical cells 12 and 13 is proportional to the amount of peracetic acid present in the sample solution and the computed result is continuously shown on the liquid crystal display 24. In addition, the spectrophotometer amplifiers 24 also produce a signal, proportional to the analysis result, which is used (via the control unit 27) to actuate the pumps 36 and 37 (preferably Nikkiso diaphragm metering pumps) which will deliver additional make-up peracetic acid to the sterilant tank in order to maintain a pre-determined concentration of peracetic acid (in this case 300 mg/l). The control unit 27 includes electronic relays and timers which ensure that a fail-safe condition will prevail in the event of any system malfunction.

Practical experience has shown that the above system is capable of maintaining a pre-set concentration of peracetic acid of 300 mg/l to within 10 mg/l over long periods of continuous operation.

As mentioned above, the sample stream can be split either before or after it has been mixed with the colorimetric reagent. The former embodiment is illustrated in FIG. 1 and the latter embodiment is illustrated in FIG. 3 in which sample 2' is mixed with colorimetric reagent 3' in a suitable mixing device which may be in the form of a mixing coil 41. A peristaltic pump 1' may be used to meter both the sample and reagent flows. Thereafter, the stream is split into two streams 5' and 7'. Stream 5' is heated in heater 11' to effect reaction between the colorimetric reagent and any peroxycompound present in the sample. Differential colorimetric reaction is then effected at 12' and 13' on the heated and unheated streams as described above in connection with FIGS. 1 and 2.

I claim:

1. A continuous process for the analysis of a sample of a body of liquid containing a peroxycompound and hydrogen peroxide by a colorimetric technique, comprising the following steps (a)–(e):
    (a) continuously taking a sample from said body of liquid;
    (b) continuously mixing said sample with a colorimetric reagent to provide a mixed sample, said reagent being selected to react with the peroxycompound and the hydrogen peroxide at an elevated temperature and only with hydrogen peroxide at a lower temperature:
    (c) dividing said mixed sample into first and second streams, each of said first and second streams containing a mixture of said sample and said colorimetric reagent;
    (d) continuously heating said first stream to said elevated temperature so that the peroxycompound and the hydrogen peroxide react with the colorimetric reagent whilst maintaining said second stream at said lower temperature so that only the hydrogen peroxide reacts with the colorimetric reagent; and
    (e) thereafter effecting continuous differential colorimetric analysis between said first stream after heating and said second stream to provide a differential signal, whereby said differential signal provides a measure of the concentration of the peroxycompound in said body of liquid.

2. A process according to claim 1, wherein the volume flows of said first and second streams are the same.

3. A process according to claim 1, wherein the peroxycompound comprises peracetic acid, the colorimetric reagent comprises sodium molybdate, and the elevated temperature is in the range of 90°-95° C.

4. A process according to claim 1 further comprising using said differential signal to control the addition of peroxycompound to the body of liquid from which said sample was taken.

5. Apparatus for the continuous analysis of a sample of a body of liquid containing a peroxycompound and hydrogen peroxide by a colorimetric technique comprising:
    means for continuously taking a sample from a body of liquid;
    mixing means for continuously mixing the sample with a colorimetric reagent to provide a mixed sample, the reagent being selected to react with the peroxycompound and the hydrogen peroxide at an elevated temperature and only with hydrogen peroxide at a lower temperature;
    means for dividing the mixed sample into first and second streams, each of the first and second streams containing a mixture of the sample and the colorimetric reagent;
    means for continuously heating the first stream to said elevated temperature so that the peroxycompound and the hydrogen peroxide react with the colorimetric reagent;
    means for maintaining the second stream at said lower temperature so that only the hydrogen peroxide reacts with the colorimetric reagent; and
    means for effecting continuous differential colorimetric analysis between the first stream after heating and the second stream to provide a differential signal, whereby said differential signal provides a measure of the concentration of the peroxycompound.

6. Apparatus according to claim 5, further comprising means to derive a control signal from said differential signal, and means to use said control signal to control the addition of peroxycompound to the body of liquid.

7. Apparatus according to claim 5, wherein said means for taking a sample comprises a peristaltic pump.

8. Apparatus according to claim 7, wherein said peristaltic pump further comprises means for metering a predetermined quantity of the colorimetric reagent to said mixing means for mixing with the said sample.

9. A continuous process for the analysis of a sample of a body of liquid containing a peroxycompound and hydrogen peroxide by a colorimetric technique, comprising the following steps (a)–(e):
   (a) continuously taking a sample from said body of liquid;
   (b) dividing said sample into at least two streams;
   (c) continuously mixing each of said at least two streams with a colorimetric reagent to provide at least first and second streams each containing a mixture of said sample and said colorimetric reagent, said colorimetric reagent being selected to react with the peroxycompound and the hydrogen peroxide at an elevated temperature and only with hydrogen peroxide at a lower temperature;
   (d) continuously heating said first stream to said elevated temperature so that the peroxycompounp and the hydrogen peroxide react with the colorimetric reagent whilst maintaining said second stream at said lower temperature so that only the hydrogen peroxide reacts with the colorimetric reagent; and
   (e) thereafter effecting continuous differential colorimetric analysis between said first stream after heating and said second stream to provide a differential signal, whereby said differential signal provides a measure of the concentration of the peroxycompound in said body of liquid.

10. A process according to claim 9, wherein the volume flows of said first and second streams are the same.

11. A process according to claim 9, wherein the peroxycompound comprises peracetic acid, the colorimetric reagent comprises sodium molybdate, and the elevated temperature is in the range of 90°–95° C.

12. A process according to claim 9 wherein step (b) comprises dividing said sample into three streams and wherein step (c) further comprises continuously mixing the third of said three streams with a diluent free of said colorimetric reagent, and wherein said process further comprises effecting differential colorimetric analysis between said second and third streams to provide a further differential signal, whereby said further differential signal provides a measure of the concentration of hydrogen peroxide in said body of liquid.

13. A process according to claim 9 further comprising using said differential signal to control the addition of peroxycompound to the body of liquid from which said sample was taken.

14. Apparatus for the continuous analysis of a sample of a body of liquid containing a peroxycompound and hydrogen peroxide by a colorimetric technique comprising:

means for continuously taking a sample from a body of liquid;
   means for dividing the sample into at least two streams;
   mixing means for continuously mixing each of the at least two streams with a colorimetric reagent to provide first and second streams each containing a mixture of the sample and the colorimetric reagent, the reagent being selected to react with the peroxycompound and the hydrogen peroxide at an elevated temperature and only with hydrogen peroxide at a lower temperature;
   means for continuously heating the first stream to said elevated temperature so that the peroxycompound and the hydrogen peroxide react with the colorimetric reagent;
   means for maintaining the second stream at said lower temperature so that only the hydrogen peroxide reacts with the colorimetric reagent; and
   means for effecting continuous differential colorimetric analysis between the first stream after heating and the second stream to provide a differential signal, whereby said differential signal provides a measure of the concentration of the peroxycompound.

15. Apparatus according to claim 14 further comprising means to derive a control signal from said differential signal, and means to use said control signal to control the addition of peroxycompound to the body of liquid.

16. Apparatus according to claim 14 wherein said means for dividing the sample comprises a peristaltic pump.

17. Apparatus according to claim 16 wherein said peristaltic pump further comprises means for metering a predetermined quantity of the colorimetric reagent to said mixing means for mixing with the at least two streams.

18. Apparatus according to claim 17, wherein said peristaltic pump has four ports, two for the sample and two for the colorimetric reagent and wherein said mixing means is located downstream of said pump.

19. Apparatus according to claim 17 wherein said peristaltic pump has six ports, three for the sample, two for the colorimetric reagent, and one for a diluent, and wherein said apparatus further comprises means for supplying a diluent to said pump, and means for effecting differential colorimetric analysis between the second and third streams to provide a further differential signal, whereby said further differential signal provides a measure of the concentration of hydrogen peroxide in the body of liquid.

* * * * *